United States Patent
Brieske et al.

(10) Patent No.: US 8,568,347 B2
(45) Date of Patent: Oct. 29, 2013

(54) APPARATUS FOR MAKING EXTRACORPOREAL BLOOD CIRCULATION AVAILABLE

(75) Inventors: Gerhard Brieske, Ampfing (DE); Michael Brieske, Ampfing (DE)

(73) Assignee: ZOLL LifeBridge GmbH, Ampfing (DE)

(*) Notice: Subject to any disclaimer, the term of this patent is extended or adjusted under 35 U.S.C. 154(b) by 0 days.

(21) Appl. No.: 13/466,899

(22) Filed: May 8, 2012

(65) Prior Publication Data

US 2012/0220916 A1    Aug. 30, 2012

Related U.S. Application Data

(62) Division of application No. 11/554,524, filed on Oct. 30, 2006, now Pat. No. 8,187,214.

(51) Int. Cl.
*A61M 37/00* (2006.01)

(52) U.S. Cl.
USPC .......... 604/6.16; 604/4.01; 604/6.09

(58) Field of Classification Search
USPC ............. 422/44–48; 604/4.01–6.16; 600/19
See application file for complete search history.

(56) References Cited

U.S. PATENT DOCUMENTS

| | | |
|---|---|---|
| 3,567,028 A | 3/1971 | Nose |
| 3,744,762 A | 7/1973 | Schlicht |
| 4,562,984 A | 1/1986 | Sherlock et al. |
| 4,612,170 A | 9/1986 | Luther |
| 4,876,066 A | 10/1989 | Bringham et al. |
| 5,188,604 A * | 2/1993 | Orth .............................. 604/153 |
| 5,232,437 A | 8/1993 | Lysaght et al. |
| 5,350,357 A | 9/1994 | Kamen et al. |
| 5,950,670 A | 9/1999 | Flaim |
| 6,071,257 A | 6/2000 | Stojanovic |
| 6,071,258 A | 6/2000 | Dalke et al. |
| 6,224,829 B1 | 5/2001 | Piplani et al. |
| 6,306,346 B1 | 10/2001 | Lindsay |
| 6,695,803 B1 | 2/2004 | Robinson et al. |

(Continued)

FOREIGN PATENT DOCUMENTS

| | | |
|---|---|---|
| DE | 1284044 | 11/1968 |
| DE | 2138513 | 3/1972 |

(Continued)

OTHER PUBLICATIONS

United States Patent and Trademark Office, Notice of Allowance mailed Oct. 4, 2010 in U.S. Appl. No. 11/284,515, 8 pages.

(Continued)

*Primary Examiner* — Philip R Wiest
(74) *Attorney, Agent, or Firm* — Robert D. Buyan; Stout, Uxa, Buyan & Mullins, LLP

(57) ABSTRACT

The present invention relates to an apparatus for making extracorporeal blood circulation available, in particular a heart-lung machine, comprising a venous connection and an arterial connection, between which a blood reservoir, a blood pump and a bubble detector for the detection of air bubbles are provided, with, downstream of the bubble detector, an arterial line leading to the arterial connection via an arterial clamp and a bypass leading via a bypass clamp back into the blood reservoir which is connected to a pump extracting air from the blood reservoir. In addition, the present invention relates to a method of operating such an apparatus.

21 Claims, 1 Drawing Sheet

(56) References Cited

U.S. PATENT DOCUMENTS

| | | | |
|---|---|---|---|
| 6,730,267 B2 * | 5/2004 | Stringer et al. | 422/45 |
| 6,748,815 B2 | 6/2004 | Povey et al. | |
| 7,022,099 B2 | 4/2006 | Litzie et al. | |
| 7,367,540 B2 | 5/2008 | Brieske | |
| 7,485,260 B2 | 2/2009 | Tamari | |
| 7,541,000 B2 | 6/2009 | Stringer et al. | |
| 7,597,546 B2 | 10/2009 | Brieske | |
| 7,682,327 B2 | 3/2010 | Kirchhof | |
| 7,824,848 B2 | 11/2010 | Owen et al. | |
| 7,846,122 B2 | 12/2010 | Brieske | |
| 2007/0146342 A1 | 6/2007 | Medler et al. | |
| 2008/0171960 A1 | 7/2008 | Brieske et al. | |

FOREIGN PATENT DOCUMENTS

| | | |
|---|---|---|
| DE | 3834952 | 4/1989 |
| DE | 19534502 | 3/1997 |
| DE | 29719899 | 1/1998 |
| DE | 19702098 | 7/1998 |
| DE | 19905937 | 7/2000 |
| EP | 0171749 | 2/1986 |
| EP | 0223864 | 6/1987 |
| EP | 1661592 | 5/2006 |
| FR | 2368284 | 5/1978 |
| JP | 2002527212 | 8/2002 |
| JP | 2002536126 | 10/2002 |
| JP | 2003180824 | 7/2003 |
| WO | WO95/11709 | 5/1995 |
| WO | WO02/26288 | 4/2002 |
| WO | WO2004/098678 | 11/2004 |

OTHER PUBLICATIONS

United States Patent and Trademark Office, Office Action mailed Apr. 21, 2010 in U.S. Appl. No. 11/284,515, 11 pages.

Japanese Patent Office, Examiner's Report mailed Dec. 22, 2009 in Australian Patent Application No. JP2005-335622, 4 pages.

United States Patent and Trademark Office, Final Office Action mailed Dec. 8, 2009 in U.S. Appl. No. 11/284,515, 10 pages.

United States Patent and Trademark Office, Office Action mailed May 27, 2009 in U.S. Appl. No. 11/284,515, 13 pages.

European Patent Office, Decision to Grant dated May 6, 2008 in European Patent Application No. EP04027855.8-2310/1661592, 2 pages.

European Patent Office, European Search Report dated Aug. 10, 2007 in European Patent Application No. EP07010455.9-2310, 7 pages.

European Patent Office, Translation of European Search Report dated Apr. 20, 2005 in European Patent Application No. EP04027855.8, 4 pages.

* cited by examiner

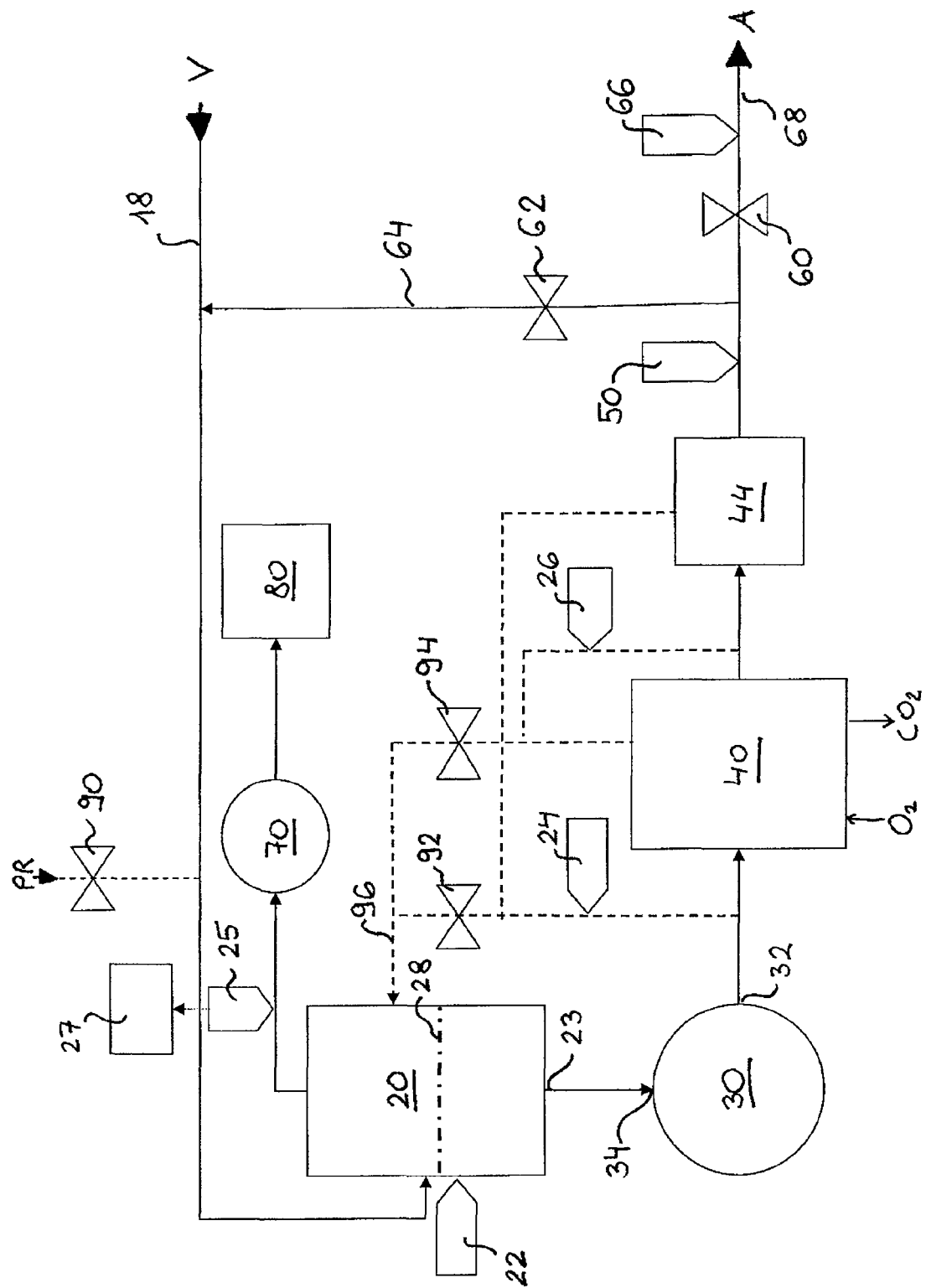

APPARATUS FOR MAKING EXTRACORPOREAL BLOOD CIRCULATION AVAILABLE

RELATED APPLICATIONS

This application is a divisional of and claims priority to U.S. patent application Ser. No. 11/554,524 filed Oct. 30, 2006 now U.S. Pat. No. 8,187,214 entitled Apparatus For Making Extracorporeal Blood Circulation Available, which is hereby incorporated herein by reference in its entirety.

FIELD OF THE INVENTION

The present invention relates to an apparatus for making extracorporeal blood circulation available, in particular a so-called heart-lung machine. Apparatus of this type can replace the pump function of the heart and the lung function for a limited period of time. The blood of the patent is introduced via a venous connection into the extracorporeal blood circuit and is pumped by a blood pump via different blood-conducting components to an arterial connection from where the blood is again pumped into the patient's blood circulation.

BACKGROUND

When such an extracorporeal blood circuit is used, air bubbles may form inside the blood circuit. In addition, air which was included in the blood circuit on the putting into operation of the extracorporeal blood circuit can enter into the blood. An air bubble which enters into the patient's blood circulation can cause a fatal air embolism in the worst case.

This problem has been known for some time and there are different strategies to avoid air bubbles being located in the blood exiting the extracorporeal blood circuit via the arterial connection. There are, for example, air bubble detectors which can detect air bubbles in the blood stream. With the previously known systems, a visual or acoustic alarm signal is output on detection of an air bubble and the blood supply to the patient is stopped. Subsequently, the medical personnel on hand must act as fast as possible since the problem has to be eliminated and the patent has to be treated further. Equally, different components are known which should filter air bubbles out of the blood, for example blood filters which collect and retain both particles and gas bubbles.

SUMMARY

It is the object of the present invention to further reduce the risk of the occurrence of air embolisms in the operation of apparatus of the initially named kind. In this connection, human intervention should not be necessary if at all possible.

This object is satisfied by the apparatus in accordance with the independent apparatus claims and by the corresponding methods in accordance with the independent method claims.

In accordance with the invention, a blood reservoir, a blood pump which replaces the pump function of the heart, and a bubble detector for the detection of air bubbles are provided between the venous connection and the arterial connection. The blood entering at the venous connection is pumped by the blood pump through the blood reservoir and, optionally, through further blood-conducting components via the bubble detector up to the arterial connection. Downstream of the bubble detector, an arterial line which can be closed by an arterial clamp leads to the arterial connection via which the blood is again conducted into the patient's blood circulation. If the bubble detector detects an air bubble, the arterial clamp can be closed immediately so that the air bubble cannot enter into the patient's blood circulation. At the same time, a bypass clamp is opened so that the blood is guided back into the blood reservoir through a bypass. The blood reservoir is connected to a further pump which can actively extract air from the blood reservoir. The air bubbles rising upwardly in the blood reservoir are extracted by this pump and, as soon as the bubble detector no longer detects any air bubbles, the arterial clamp is opened again and the bypass clamp is closed again.

It is ensured by a sufficiently long reaction path between the bubble detector and the arterial clamp and by a short reaction tie of the arterial clamp, which is preferably a fast-closing clamp such as is described in U.S. patent application Ser. No. 11/366,914 (now U.S. Pat. No. 7,367,540) that the detected air bubble cannot flow through the arterial clamp to the arterial connection before said arterial clamp closed.

The apparatus in accordance with the invention therefore reacts automatically to the detection of an air bubble and eliminates it. As soon as the air bubble has been eliminated, the patient is again supplied with blood as before without any human intervention having been necessary. This in particular increases safety with a portable device for the provision of an extracorporeal blood circuit such as is described in U.S. patent application Ser. Nos. 11/284,515 and 10/839,126 (now U.S. Pat. Nos. 7,846,122 and 7,682,327 respectively), whose disclosure is made part of this application by reference. The emergency physician must only connect the patient properly to the apparatus in accordance with the invention and can then dedicate himself to the further medical care of the patient, while the apparatus eliminates the risk of an air embolism with high probability without human intervention.

Advantageous embodiments of the present invention are described in the dependent claims and in the now following description.

In accordance with an advantageous embodiment of the invention, an oxygenator which enriches the blood with oxygen and thus takes over the function of the lung is arranged between the blood pump and the bubble detector. The oxygenator likewise contributes to the elimination of any air bubbles present since these are held back at the membrane present in the oxygenators used today. An arterial filter which collects and holds back microparticles which have entered into the blood as well as gas bubbles can furthermore be provided in front of the bubble detector.

It is particularly advantageous for blood-conducting components of the apparatus such as an oxygenator or an arterial filter to be connected to the blood reservoir via a venting line. The venting line can in this connection be closed by venting clamps and primarily serves for flushing and venting during a priming process before the actual putting into operation of the apparatus. The venting clamps can, however, also be opened briefly during the operation of the apparatus at regular time intervals so that air which has collected in the blood-conducting components is introduced into the reservoir. The air then rises to the surface in the reservoir and can be extracted by the pump provided for this purpose. The venting line is connected to the blood-conducting components in each case at their side disposed upwardly in operation so that upwardly rising air bubbles migrate into the venting line. A saturation of the blood-conducting components with air is avoided by this regular venting and the risk of an air bubble moving up to the bubble detector at all is reduced.

In accordance with a further advantageous embodiment of the invention, the blood pump is made as a centrifugal pump. Since centrifugal pumps cannot transport any real air volumes, the probability that the blood exiting the apparatus contains air bubbles is further reduced simply by the use of a centrifugal pump. In addition, the centrifugal pump can be provided with a central inlet and a tangential outlet, with the tangential outlet advantageously being arranged such that it faces downwardly when the apparatus is in an operation position. Since any air bubbles present in the pump head rise upwardly, the probability of the transport of air bubbles is further reduced by this geometry.

The pump extracting the air from the blood reservoir is preferably a roller pump which can additionally have a clamping function. Such a pump is described in U.S. patent application Ser. No. 11/366,342 and permits the extraction of air from the blood reservoir with simple means, with it being ensured by the clamping function that no air can flow in the opposite direction, i.e. into the reservoir, even when the pump is switched off.

In accordance with an advantageous embodiment of the invention, an air container is arranged downstream of this pump extracting air from the blood reservoir and the air extracted from the reservoir is pumped into it. The total extracorporeal blood circuit thereby remains closed toward the outside. A simple plastic pouch can serve as the air container.

Additional protection from air bubbles in the blood exiting the apparatus can be achieved in that the blood reservoir is split up into an inlet region and an outlet region by a membrane permeable for blood, but impermeable for air bubbles.

In accordance with a further advantageous embodiment of the invention, means are provided for the monitoring of the filling level of the blood reservoir. A first sensor is preferably provided which detects whether the filling level reaches a first threshold value. A second sensor detects whether the filling level falls below a second threshold value lying below the first threshold value. The corresponding information can be passed on to an electronic control unit of the apparatus so that, on a falling below of the first threshold value, the pump can be switched on to extract air from the blood reservoir. The air which collects in the blood reservoir in bypass operation after detection of an air bubble or on a regular venting of blood-conducting components is thus extracted automatically as soon as a certain air amount is present in the reservoir. As further security, the blood pump can be switched off if the filling level falls below the second threshold value. In this case, an alarm signal is simultaneously output. It is possible for the filling level of the reservoir to fall below the second threshold value, for example, if the venous connection is not properly connected to the patient's blood circulation, but has become loose so that only air is sucked through. In such cases, the blood pump is switched off immediately thanks to the described filling level monitoring.

In accordance with a further advantageous embodiment of the invention, the bypass clamp is opened at regular time intervals for a short period to flush the bypass. It is thereby avoided that blood standing in the bypass in front of the closed bypass clamp coagulates and that this coagulated blood then enters into the extracorporeal blood circuit after the opening of the bypass clamp and, in the worst case, subsequently via the arterial connection into the patient's blood circulation.

The probability that an air bubble enters into the patient's blood circulation and triggers an air embolism is considerably lowered by the interaction of the described features. An intervention of the trained medical staff due to an error report is only necessary in an extreme emergency. In the normal case, the apparatus in accordance with the invention can successfully prevent air bubbles entering into the blood circulation of the patient connected to the apparatus without any human intervention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The invention should be described in more detail in the following with reference to a preferred embodiment and to the enclosed FIGURE.

The enclosed FIG. 1 shows a schematic representation of the individual components of a heart-lung machine.

DETAILED DESCRIPTION

The following description of the preferred embodiment is merely exemplary in nature and is in no way intended to limit the invention, its application, or uses.

The patient blood coming from a venous connection V is guided via a line 18 into a blood reservoir 20 and moves from there via an outlet 23 into an inlet 34 of a centrifugal pump 30. The inlet 34 is arranged centrally at a pump head of the centrifugal pump 30. The blood is pumped via a tangential outlet 32 arranged at the bottommost point of the pump head of the centrifugal pump 30 into an oxygenator 40 to which an oxygen supply line is connected. The blood enriched with oxygen is subsequently filtered in an arterial filter 44 and finally flows, in the normal case, through an arterial line 68 via the arterial connection A back into the body of the patient.

The blood reservoir 20 is split into an inlet region (at the top in FIG. 1) and an outlet region (at the bottom in FIG. 1) by a membrane 28. The membrane 28 is permeable for blood, but prevents air bubbles entering into the outlet region from the inlet region.

A bubble detector 50 is arranged between the arterial filter 44 and the arterial connection A. As long as it does not detect any air bubbles, an arterial clamp 60 in the arterial line 68 remains open, while a bypass clamp 62 remains closed. A throughflow sensor 66 measures the blood flow in the arterial line 68 so that said blood flow can be constantly monitored.

If an air bubble is detected in the bubble detector 50, the arterial clamp 60 is closed immediately. The reaction path between the bubble detector 50 and the arterial clamp is so long that the detected air bubble only reaches the clamp when this has already been closed. The clamp 60 is a fast-closing clamp which closes in less than 300 ms. Such a fast-closing clamp is described in U.S. patent application Ser. No. 11/366, 914 to which reference is herewith made. It can be precluded by the sufficiently long reaction path and the fast closing of the clamp that the air bubble detected in the bubble detector 50 can reach up to the arterial connection A before the closing of the clamp 60.

At the same time, the bypass line 62 is opened so that the blood, together with the detected air bubble, flows via a bypass 64 back into the line 18 and into the blood reservoir 20.

In the blood reservoir 20, air bubbles rise upwardly so that the blood is located at the bottom in the reservoir, while air collects at the top. Means 22 for the monitoring of the filling level of the blood reservoir are electronically coupled to a roller pump 70 for the extraction of air from the reservoir, for example via an electronic control unit. As soon as the means 22 for the monitoring of the filling level of the blood reservoir 20 report that the filling level has fallen below a first threshold value, the roller pump 70 is switched on, extracts the air present at the top in the reservoir 20 and pumps it into an air container 80. The roller pump 70 has a clamping function so that it acts as a clamp if it is not actively pumping and prevents a backflow of air into the blood reservoir 20.

If the filling level of the blood reservoir falls further despite the pumping away of air by the roller pump 70 and if it falls below a second threshold value, for example because the venous connection V is not properly connected, the centrifugal pump 30 is switched off and an alarm signal is output.

The oxygenator 40 and the arterial filter are each connected to the upper region of the blood reservoir 20 not filled with blood via a venting line 96 provided with venting valves 92, 94. The venting line first serves for the flushing and venting of the heart-lung machine during a priming procedure before its putting into operation. In this connection, a so-called priming liquid is filled in via a priming connection PR and the extracorporeal blood circuit is vented. The priming circuit is shown by broken lines in FIG. 1. The venting clamps 92 and 94 are normally closed during the operation of the heart-lung machine. They are, however, opened briefly at regular time intervals, for example every 10 to 15 minutes, so that air which has collected in the oxygenator or the arterial filter is guided into the reservoir 20 and can be extracted from there.

The reference numerals 24 and 26 designate pressure sensors which monitor the pressure before and after the oxygenator. The measured values of the pressure sensors are forwarded to a pressure monitoring unit 27 via a connection not shown in FIG. 1 for reasons of clarity. In the event of an unusually increasing pressure drop at the oxygenator 40, this can be clogged by coagulated blood so that there is a need for action.

In addition, the extraction pressure at which blood is extracted from the patient into the line 18 is monitored with the aid of a pressure sensor 25. In this connection, the line anyway present between the blood reservoir 20 and the roller pump 70 is utilized to measure this pressure. The measured result is likewise passed on to the pressure monitoring unit 27.

To avoid blood standing in the bypass 64 in FIG. 1 beneath the bypass clamp 62 coagulating while the arterial clamp 60 is open and the bypass clamp 62 is closed, the bypass clamp 62 is opened at regular time intervals for a short period. The bypass 64 is periodically flushed in this manner so that blood coagulation cannot occur in the bypass 64.

The description of the invention is merely exemplary in nature and, thus, variations that do not depart from the gist of the invention are intended to be within the scope of the invention. Such variations are not to be regarded as a departure from the spirit and scope of the invention.

REFERENCE NUMERAL LIST

18 line
20 blood reservoir
22 means for monitoring the filling level
23 outlet, blood reservoir
24, 25, 26 pressure sensor
27 pressure monitoring unit
28 membrane
30 blood pump
32 tangential outlet
34 central inlet
40 oxygenator
44 arterial filter
50 bubble detector
60 arterial clamp
62 bypass clamp
64 bypass
66 flow sensor
68 arterial line
70 roller pump
80 air container
90 inlet clamp
92, 94 venting clamps
96 venting line
V venous connection
A arterial connection
PR connection for priming liquid

What is claimed is:

1. An apparatus for making extracorporeal blood circulation available comprising a venous connection and an arterial connection, between which a blood reservoir, a blood pump and a bubble detector for the detection of air bubbles are provided, with, downstream of the bubble detector, an arterial line leading to the arterial connection via an arterial clamp and a bypass leading via a bypass clamp back into the blood reservoir which is connected to a pump extracting air from the blood reservoir.

2. An apparatus in accordance with claim 1, wherein at least one of an oxygenator and an arterial filter is provided between the blood pump and the bubble detector.

3. An apparatus in accordance with claim 1, wherein blood-conducting components of the apparatus, in particular at least one of an oxygenator and an arterial filter, are connected to the blood reservoir via a venting line, with venting clamps being respectively provided between the blood-conducting components and the blood reservoir for the closing of the venting line.

4. An apparatus in accordance with claim 1, wherein the blood pump is made as a centrifugal pump with a central inlet and a tangential outlet, with the tangential outlet facing downwardly when the apparatus is in an operating position.

5. An apparatus in accordance with claim 1, wherein the pump extracting air from the blood reservoir is a roller pump.

6. An apparatus in accordance with claim 5 wherein the roller pump has a clamping function.

7. An apparatus in accordance with claim 1, wherein an air container is arranged downstream of the pump extracting air from the blood reservoir.

8. An apparatus in accordance with claim 1, wherein the blood reservoir is split into an inlet region and an outlet region by a membrane impermeable for air bubbles.

9. An apparatus in accordance with claim 1, wherein means are provided for the monitoring of the filling level of the blood reservoir.

10. The apparatus of claim 1 wherein the blood reservoir comprises a membrane impermeable to air.

11. The apparatus of claim 1 wherein the blood reservoir comprises a blood level sensor.

12. The apparatus of claim 1 wherein the pump comprises a centrifugal pump.

13. The apparatus of claim 1 wherein the pump comprises an inlet arranged centrally at a pump head.

14. The apparatus of claim 1 wherein the pump comprises a centrifugal pump with a tangential outlet facing downwardly when the apparatus is in an operating position.

15. The apparatus of claim 1 further comprising an oxygenator connected to the fluid line between the blood reservoir and the arterial connection.

16. The apparatus of claim 15 further comprising a venting line connecting the oxygenator to the blood reservoir.

17. The apparatus of claim 1 further comprising an arterial filter connected to the fluid line between the blood reservoir and the arterial connection.

18. The apparatus of claim 16 further comprising a venting line connecting the arterial filter to the blood reservoir.

19. The apparatus of claim 1 further comprising an air extraction pump connected to the blood reservoir.

20. An apparatus for making extracorporeal blood circulation available comprising a venous connection and an arterial connection, between which a blood reservoir split into an inlet region and an outlet region by a membrane impermeable for air bubbles and having means for the monitoring of the filling level, a blood pump made as a centrifugal pump, an oxygenator, an arterial filter and a bubble detector for the detection of air bubbles are provided, with, downstream of the bubble detector, an arterial line leading to the arterial connection via an arterial clamp and a bypass leading via a bypass clamp back into the blood reservoir which is connected to a roller pump conveying air from the blood reservoir into an air container.

21. An apparatus for making extracorporeal blood circulation available comprising:
- a fluid line connecting a venous connection to a arterial connection;
- a blood reservoir connected to the fluid line between the venous connection and the arterial connection;
- a pump connected to the fluid line between the blood reservoir and the arterial connection;
- a bubble detector connected to the fluid line between the blood reservoir and the arterial connection;
- a bypass line comprising a bypass clamp, a first end of the bypass line connected to the fluid line between the bubble detector and the arterial connection and a second end of the bypass line connected to the fluid line between the venous connection and the blood reservoir; and
- an arterial clamp connected to the fluid line between the first end of the bypass line and the arterial connection.

\* \* \* \* \*